United States Patent
Thoret Bauchet

(10) Patent No.: US 12,319,650 B2
(45) Date of Patent: Jun. 3, 2025

(54) CLEANING PROCESS OF A VINYL AROMATIC COMPOUNDS DISTILLATION UNIT AND PROCESSES INCLUDING SUCH CLEANING PROCESS

(71) Applicant: TOTALENERGIES ONETECH, Courbevoie (FR)

(72) Inventor: Jean-Pierre Thoret Bauchet, Brussels (BE)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

(21) Appl. No.: 18/837,937

(22) PCT Filed: Feb. 21, 2023

(86) PCT No.: PCT/EP2023/054298
§ 371 (c)(1),
(2) Date: Aug. 13, 2024

(87) PCT Pub. No.: WO2023/161222
PCT Pub. Date: Aug. 31, 2023

(65) Prior Publication Data
US 2025/0109083 A1  Apr. 3, 2025

(30) Foreign Application Priority Data
Feb. 23, 2022 (EP) .................................. 22315038

(51) Int. Cl.
C07C 7/04 (2006.01)
C07C 5/333 (2006.01)

(52) U.S. Cl.
CPC ............... *C07C 7/04* (2013.01); *C07C 5/333* (2013.01); *C07C 2529/08* (2013.01); *C07C 2529/18* (2013.01)

(58) Field of Classification Search
CPC ....... C07C 7/04; C07C 5/333; C07C 2529/08; C07C 2529/18
See application file for complete search history.

(56) References Cited

U.S. PATENT DOCUMENTS

| 3,476,656 A | 11/1969 | Tassell et al. |
| 4,654,450 A | 3/1987 | Miller |
| 2019/0337877 A1* | 11/2019 | Treleaven ................. C07C 7/04 |

FOREIGN PATENT DOCUMENTS

| CN | 101056832 A | 10/2007 |
| CN | 103664498 A | 3/2024 |

(Continued)

OTHER PUBLICATIONS

International Search Report and Written Opinion issued in Application No. PCT/EP2023/054298, dated May 16, 2023, 8 pages.

(Continued)

*Primary Examiner* — Thuan D Dang
(74) *Attorney, Agent, or Firm* — Ewing & Jones, PLLC

(57) ABSTRACT

The disclosure relates to a cleaning process of a vinyl aromatic compounds distillation unit wherein the vinyl aromatic compounds distillation unit comprises one or more distillation columns, the process comprises a step of cleaning one or more distillation columns followed by a step of passivation of at least one distillation column wherein a flux comprising a passivation mixture is passed through at least one distillation column under passivation conditions comprising a temperature of at least 90° C., wherein the passivation mixture comprises a component A being one or more polymerisation inhibitors; and a component B selected from steam and/or one or more hydrocarbons devoid of vinyl group. The disclosure also relates to the process of purification and of production of one or more vinyl aromatic compounds that include the said cleaning process.

20 Claims, 2 Drawing Sheets

(56) References Cited

FOREIGN PATENT DOCUMENTS

| | | | |
|---|---|---|---|
| JP | 2003096012 A | * | 4/2003 |
| KR | 101299781 B1 | | 8/2013 |
| WO | 00/14039 A1 | | 3/2000 |
| WO | 2014129711 A1 | | 8/2014 |

OTHER PUBLICATIONS

International Preliminary Report on Patentability issued in Application No. PCT/EP2023/054298, dated Aug. 27, 2024, 6 pages.
Muhler M., et al., "The nature of the iron oxide-based catalyst for dehydrogenation of ethylbenzene to styrene, 2. Surface chemistry of the active phase", J. of Cata., 1992, 138, 413-44.
Ch. Baerlocher et al., "Atlas of Zeolite Framework Types", 6th revised edition, 2007, Elsevier, 405 pages.
Chinese Office Action issued in Application No. 202380022975.1, dated Jan. 25, 2025, 18 pages.

* cited by examiner

CLEANING PROCESS OF A VINYL AROMATIC COMPOUNDS DISTILLATION UNIT AND PROCESSES INCLUDING SUCH CLEANING PROCESS

CROSS-REFERENCE TO RELATED APPLICATIONS

This application claims the benefit of PCT/EP2023/054298 filed Feb. 21, 2023, which claims priority from EP 22315038.4 filed Feb. 23, 2022, which are incorporated herein by reference in their entireties for all purposes.

TECHNICAL FIELD

The present disclosure relates to a process for treating a distillation column suitable for distilling vinyl aromatic compounds, a process of purification of at least one vinyl aromatic compound and to a process for the production of a vinyl aromatic compound from the corresponding saturated aromatic compound, in particular for the production of styrene from ethylbenzene.

TECHNICAL BACKGROUND

Distillation units are prone to fouling by polymers when the component to be distilled comprises polymerizable group, such as a vinyl group. For example, in the case of the purification of styrene, the presence of divinylbenzene can clog the distillation column upon polymerization. After maintenance for cleaning, it always remains living chain polymer residues which act as polymer seeds. When the distillation unit is restarted, these polymer seeds are reactivated and fouling restarts, leading to a decrease in the efficiency of the distillation.

U.S. Pat. No. 3,476,656 discloses that since styrene tends to undergo polymerization by application of heat, it is possible to use various styrene polymerization inhibitors, such as molten sulphur, tert-butyl catechol (TBC). Other styrene polymerization inhibitors such as diethyl-hydroxylamine (DEHA), phenyl-p-phenylenediamines and phenothiazines can be used. However, the use of polymer inhibitors during distillation has a cost and a solution to reduce these costs is still to be found.

WO 00/14039 discloses a composition that is suitable for inhibiting the polymerization of vinyl aromatic compounds. The such composition comprises a di-hydroxy-arene, a hydrogen transfer agent and a stable nitroxide.

These components are used during the purification of the styrene by distillation technique so that the level of polymerization is kept low. However, once the styrene distillation units are stopped, the styrene distillation column still comprises the polymer seeds.

To this respect, KR101299781 discloses a method for cleaning an internal component of a fractionating column or a distillation column which is applicable for fractionating, refining and distillation processes of petrochemical substance. The method uses ultrasound to bring the substance to be cleaned into contact with a cleaning solution comprising isopropyl alcohol. This physical clearing, due to the ultrasound vibrations, cannot thoroughly clean the distillation column.

With respect to heat exchangers, thermal cleaning has been developed to replace traditional high-pressure cleaning. Using high-pressure cleaning has indeed the drawback that the jet of water does not reach every nook and cranny around the heat exchanger, leaving subsequently dirt/dust. By contrast, using thermal cleaning allows for the restoration of the heat exchanger to deliver its original performance.

The objective of the disclosure is thus to provide a way to clean efficiently the distillation units of vinyl aromatic compounds, in particular the distillation units of styrene.

SUMMARY

According to a first aspect, the disclosure provides a cleaning process of a vinyl aromatic compounds distillation unit wherein the vinyl aromatic compounds distillation unit comprises one or more distillation columns, the process comprises a step of cleaning one or more distillation columns and is remarkable in that the step of cleaning one or more distillation columns is followed by a step of passivation of at least one distillation column wherein a flux comprising a passivation mixture is passed through at least one distillation column under passivation conditions comprising a temperature of at least 90° C. and a pressure up to 300 kPa, wherein the passivation mixture comprises a component A being one or more polymerisation inhibitors and a component B selected from steam and/or one or more hydrocarbons devoid of vinyl group that are or comprise one or more aliphatic saturated hydrocarbons and/or one or more aromatic compounds.

Advantageously, the passivation mixture comprises from 0.01 wt. % to 2.0 wt. % of component A based on the total weight of the passivation mixture, the remaining being made of component B, or from 0.01 to 1.0 wt. % of component A, or from 0.01 to 0.80 wt. % of component A, or from 0.01 to 0.50 wt. % of component A, or from 0.01 to 0.10 wt. % of component A, preferably from 0.02 to 0.08 wt. % of component A, more preferably from 0.03 to 0.07 wt. % of component A.

Surprisingly, it was found that it is possible to reduce or at least keep at a low level the amount of polymer inhibitor used during the purification process of one or more vinyl aromatic compounds by chemical passivation performed during the cleaning process. Without being bound by a theory, the process of the disclosure allows the deactivation of the polymers seeds that remain in the columns after their cleaning with a passivation step. Therefore, the process provides a deactivation of the internal surface of the distillation columns during their lifetime, said deactivation being performed in the presence of polymer seeds during the cleaning process of the column when the distillation is stopped for maintenance. This finding is remarkable in that the passivation step is not only a pre-treatment of the internal surface of the columns but a regeneration of the originally passive behaviour of the said surface. The passivation step according to the disclosure chemically deactivates the polymer seeds present in the columns so that the content of polymer inhibitor used in the next distillation can be reduced or at least be kept at a low level.

It was found that the polymer seeds were stable at ambient temperatures such as the temperature used when cleaning the columns. The process of the disclosure raises the temperature to at least 90° C. using a component B to activate the polymer seeds which then react with the polymerisation inhibitors so that further polymerization during distillation is prevented. The use of polymerization inhibitors in the passivation mixture further allows passivating of the distillation columns at a temperature equal to or higher than the temperature at which the distillation is performed but without a need of providing the excess heat necessary for combustion of the polymer seeds. The process of the present disclosure is in particular efficient to treat a distillation column that has suffered from a polymerization incident, namely in which polymerization has occurred. It allows restarting the distillation unit with its original behaviour.

For example, the vinyl aromatic compounds are selected from styrene, alpha-methyl styrene, divinylbenzene, polyvinyl benzene and any mixture thereof; with preference, the vinyl aromatic compounds are or comprise styrene.

For example, the flux comprising a passivation mixture that is passed through at least one distillation column during the passivation step is devoid of vinyl aromatic compounds.

For example, the vinyl aromatic compounds are or comprise styrene, and the flux comprising a passivation mixture that is passed through at least one distillation column during the passivation step comprises ethylbenzene and/or is devoid of styrene.

For example, the step of cleaning one or more distillation columns is or comprises a mechanical cleaning; with preference, the mechanical cleaning of one or more distillation columns comprises high-pressure cleaning of one or more distillation columns.

Advantageously, the passivation conditions comprise a temperature which is ranging between a temperature being 10° C. above the boiling point of the vinyl aromatic compounds at pressure conditions and a temperature being at most 20° C. above the boiling point of the vinyl aromatic compounds at pressure conditions, or ranging between a temperature being 15° C. above the boiling point of the vinyl aromatic compounds at pressure conditions and a temperature being at most 20° C. above the boiling point of the vinyl aromatic compounds at pressure conditions.

For example, the passivation conditions comprise a temperature of at least 95° C.; for example, at least 100° C.; for example, at least 105° C.; for example, at least 110° C.; for example, at least 115° C.; for example, at least 120° C.

For example, the passivation conditions comprise a temperature of at most 250° C.; for example, at most 220° C.; for example, at most 200° C.; for example, at most 180° C.; for example, at most 160° C.; for example, at most 150° C. or at most 145° C.

For example, the passivation conditions comprise a temperature ranging from 90° C. to 250° C.; for example, from 95° C. to 220° C.; for example, from 100° C. to 200° C.; for example, from 105° C. to 180° C.; for example, from 110° C. to 160° C.; for example, from 115° C. to 150° C.; for example, from 120° C. to 145° C.

For example, the passivation conditions comprise pressure conditions up to 300 kPa, preferably ranging from 90 kPa to 200 kPa; more preferably ranging from 98 kPa to 120 kPa, for example, from 100 kPa to 115 kPa.

For example, said passivation conditions comprise a passivation time which is ranging from 1 to 24 hours; for example, from 2 to 20 hours; for example, from 3 to 18 hours; for example, from 5 to 15 hours.

For example, the step of passivation is performed under an atmosphere provided by one or more inert gases such as nitrogen and/or argon.

For example, component A comprises at least one polymerisation inhibitor selected from molten sulphur, phenyl-p-phenylenediamines, phenothiazines, tert-butyl catechol, diethyl-hydroxylamine, butylated hydroxytoluene, butylated hydroxyanisole, 4-hydroxy-2,2,6,6-tetramethylpiperidin-1-oxyl, quinone methide, 2-(3,5-di-tert-butyl-4-oxocyclohexa-2,5-dien-1-ylidene)acetonitrile, 2,6-di-tert-butyl-4-(methoxymethylene)cyclohexa-2,5-dienone, 4-benzylidene-2,6-di-tert-butylcyclohexa-2,5-dienone, and any mixture thereof; with preference selected from tert-butyl catechol, diethyl-hydroxylamine and any mixture thereof, more preferably, component A is diethyl-hydroxylamine.

In one embodiment, component B is steam.

In a second embodiment, component B is one or more hydrocarbons devoid of vinyl group wherein one or more hydrocarbons devoid of vinyl group are or comprise one or more selected from saturated hydrocarbons and/or aromatic compounds; with preference, at least one aromatic compounds devoid of vinyl group is selected from benzene, toluene, o-xylene, m-xylene, p-xylene, ethylbenzene, aliphatic a mixture benzene/ethylbenzene, and any mixture thereof. For example, the one or more aliphatic saturated hydrocarbons are one or more selected from heptane, octane, nonane, decane, and any mixture thereof. For example, when a mixture benzene/ethylbenzene is selected, said mixture comprises between 10 wt. % and 30 wt. % of benzene and between 70 wt. % and 90 wt. % of ethylbenzene based on the total weight of said mixture benzene/ethylbenzene.

In a third embodiment, component B is a mixture of steam and one or more hydrocarbons devoid of vinyl group, wherein one or more hydrocarbons devoid of vinyl group are or comprise one or more aliphatic saturated hydrocarbons and/or one or more aromatic compounds; with preference, at least one aromatic compound devoid of vinyl group is selected from benzene, toluene, o-xylene, m-xylene, p-xylene, ethylbenzene, a mixture benzene/ethylbenzene, and any mixture thereof.

According to a second aspect, the disclosure provides a process of purification of one or more vinyl aromatic compounds, the process comprising the distillation of one or more vinyl aromatic compounds using vinyl aromatic compounds distillation unit wherein the vinyl aromatic compounds distillation unit comprises one or more distillation columns, the process comprising interrupting at least one time the distillation of one or more vinyl aromatic compounds to perform a cleaning process of the vinyl aromatic compounds distillation unit, remarkable in that the cleaning process of the vinyl aromatic compounds distillation unit is according to the first aspect; with preference, the one or more vinyl aromatic compounds is or comprises styrene.

For example, the cleaning process comprises a passivation step that is conducted at a temperature higher than the temperature at which the distillation is conducted.

According to a third aspect, the disclosure provides a process of production of a vinyl aromatic compound from the corresponding saturated aromatic compound, said process is remarkable in that it comprises the following steps:
a) providing a catalytic composition comprising one or more zeolites;
b) providing a stream comprising a saturated aromatic compound;
d) contacting said stream comprising a saturated aromatic compound with said catalytic composition under dehydrogenation reaction conditions comprising a temperature of at least 550° C. to obtain a vinyl aromatic compound-rich stream;
e) performing the process of purification of at least one vinyl aromatic compound according to the second aspect on said vinyl aromatic compound-rich stream;
f) optionally, recovering the vinyl aromatic compound from the vinyl aromatic compound-rich stream.

For example, the vinyl aromatic compound produced is styrene and the corresponding saturated aromatic compound is ethylbenzene; with preference, the stream provided in step (b) further comprises di-ethylbenzene, and the process further comprises a step (c) of removing said di-ethylbenzene from said stream provided in step (b) before contacting the stream with the catalyst composition.

With preference, the one or more zeolites are selected from the group of MWW, FAU, MFI, MOR family, or zeolite beta or any mixture thereof, more preferably from the group of MWW, FAU, MFI family, or zeolite beta, or any mixture thereof.

For example, the catalytic composition further comprises at least one transition metal; with preference, the at least one transition metal is selected from Cr, Mn, Fe, Co, Ni, Cu, Zn and any mixture thereof; more preferably, the transition metal is Fe.

Advantageously, the catalytic composition further comprises in addition of said at least one transition metal at least one alkali metal; with preference, said alkali metal is selected from Li, Na, K, and Cs, more preferably the alkali metal is K.

For example, the catalytic composition is or comprises a ferrite such as a potassium ferrite, $K_2Fe_{22}O_{34}$.

For example, the catalytic composition is or comprises a ferrite, preferably a ferrite with an active surface comprising potassium iron oxide with an atomic ratio of K/Fe ranging between 1/1 and 1/11, and with preference, wherein iron is only in its trivalent state. Further information regarding an example of ferrite can be found in the study of Muhler M., et al. (*J. of Cata.*, 1992, 138, 413-44).

DETAILED DESCRIPTION

Figure 1:
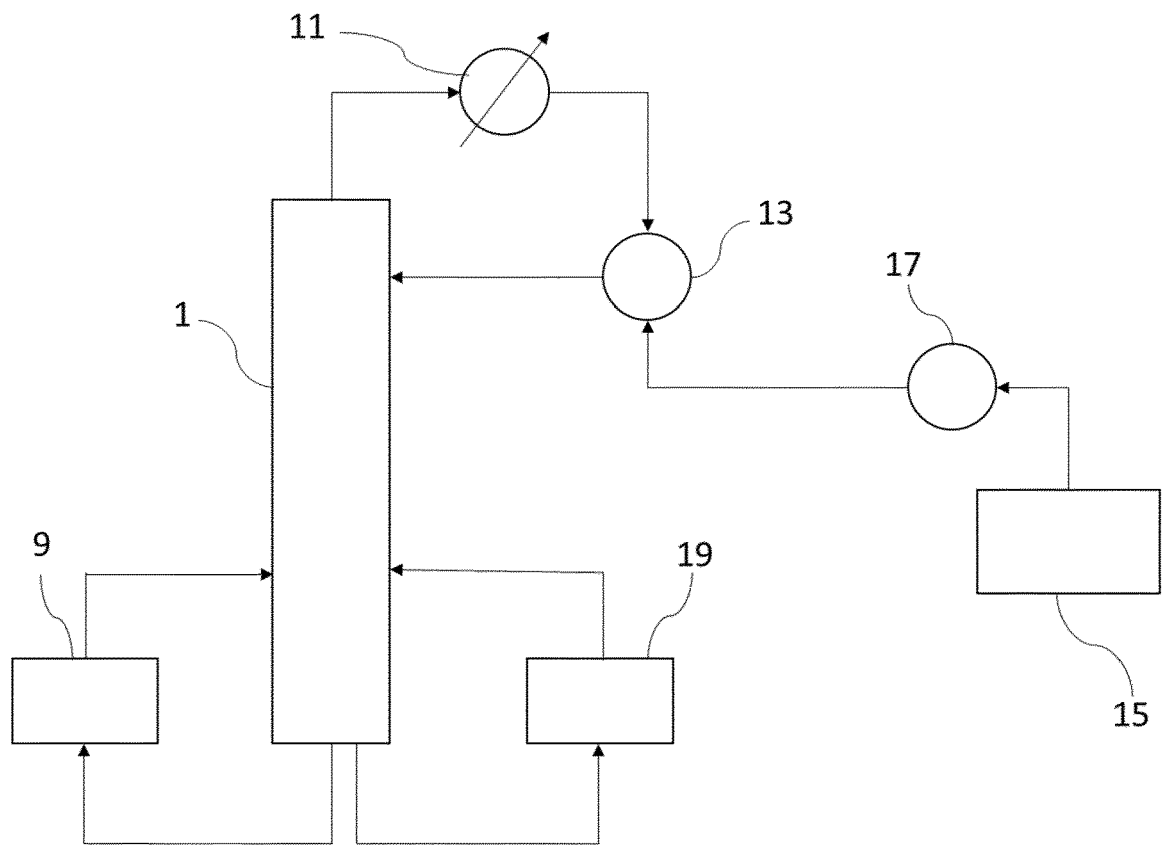
FIG. 1: Installation comprising a vinyl aromatic compounds distillation unit in accordance with the present disclosure.

For the disclosure, the following definitions are given:

Zeolite codes (e.g., CHA . . . ) are defined according to the "*Atlas of Zeolite Framework Types*", 6$^{th}$ revised edition, 2007, Elsevier, to which the present application also refers.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The term "transition metal" refers to an element whose atom has a partially filled d sub-shell, or which can give rise to cations with an incomplete d sub-shell (IUPAC definition). According to this definition, the transition metals are Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Rf, Db, Sg, Bh, Hs, Mt, Ds, Rg, and Cn.

The metals Ga, In, Sn, Tl, Pb and Bi are considered as "post-transition" metal.

The metals Au, Ag, Ru, Rh, Pd, Os, Ir and Pt show outstanding resistance to oxidation and are considered as "noble" metal. Other metal can be considered as "non-noble" metal.

The term "alkali metal" refers to an element classified as an element from group 1 of the periodic table of elements (or group IA), excluding hydrogen. According to this definition, the alkali metals are Li, Na, K, Rb, Cs and Fr.

The term "alkaline earth metal" refers to an element classified as an element from group 2 of the periodic table of elements (or group IIA). According to this definition, the alkaline earth metals are Be, Mg, Ca, Sr, Ba and Ra.

The terms "bottom" and "top" are to be understood in relation to the general orientation of the distillation unit, in particular of the vinyl aromatic compounds distillation unit. Thus, "bottom" will mean greater ground proximity than "top" along the vertical axis. In the different figures, the same references designate identical or similar elements.

The particular features, structures, characteristics or embodiments may be combined in any suitable manner, as would be apparent to a person skilled in the art from this disclosure, in one or more embodiments.

The Cleaning Process of a Vinyl Aromatic Compounds Distillation Unit

The disclosure provides a cleaning process of a vinyl aromatic compounds distillation unit wherein the vinyl aromatic compounds distillation unit comprises one or more distillation columns, the process comprises a step of cleaning one or more distillation columns 1 and is remarkable in that the step of cleaning one or more distillation columns is followed by a step of passivation of at least one distillation column 1 wherein a flux comprising a passivation mixture is passed through at least one distillation column 1 under passivation conditions comprising a temperature of at least 90° C. and a pressure up to 300 kPa, wherein the passivation mixture comprises a component A being one or more polymerisation inhibitors and a component B selected from steam and/or one or more hydrocarbons devoid of vinyl group that are or comprise one or more aliphatic saturated hydrocarbons and/or one or more aromatic compounds.

Typically, the vinyl aromatic compounds distillation unit can be as shown in FIG. 1. Said unit comprises at least one distillation column 1, the bottom of which is fluidly connected to the a reboiler loop comprising for example two reboilers (9, 19). As shown on FIG. 1, the reboilers (9, 19) are in parallel. The top of the distillation column 1 is fluidly connected to a reflux loop, the reflux loop comprising a condenser 11 upstream to a reflux drum 13, the reflux drum 13 being upstream to the distillation column 1.

The component A, that can be stored into a container 15, is injected into the reflux loop at the level of the reflux drum 13. When the component A is coming from the container 15, the line between the container 15 and the reflux drum 13 can for example comprise a pump 17. From the reflux drum 13, a flux comprising the component A is passed through the distillation column 1.

It is also possible that the component A is directly injected into the distillation column 1 and/or into the reboiler loop.

However, the component A can be injected into the reflux loop at the level of the reflux drum 13 and also directly into the distillation column 1 and/or into the reboiler loop.

In addition, a component B is passed through the distillation column 1. This can be done by injecting the component B directly at the level of the distillation column 1 and/or in the reboiler loop. Thanks to the reflux loop, the component B will be directed into the reflux loop and will therefore be mixed with the component A circulating into the reflux loop, forming subsequently a passivation mixture that will be directed into the distillation column 1 under the form of a flux.

Then, wherever the place of injection of component A, the passivation mixture always comprises the component A and the component B. In particular, the passivation mixture comprises from 0.01 wt. % to 2.0 wt. % of component A based on the total weight of the passivation mixture, the remaining being made of component B, or from 0.01 to 1.0 wt. % of component A, or from 0.01 to 0.80 wt. % of component A, or from 0.01 to 0.50 wt. % of component A, or from 0.01 to 0.10 wt. % of component A, preferably from 0.02 to 0.08 wt. % of component A, more preferably from 0.03 to 0.07 wt. % of component A.

For example, the vinyl aromatic compounds are selected from styrene, alpha-methyl styrene, divinylbenzene, polyvinyl benzene and any mixture thereof; with preference, the vinyl aromatic compounds are or comprise styrene.

For example, the flux comprising a passivation mixture that is passed through at least one distillation column during the passivation step is devoid of vinyl aromatic compounds. The use of a mixture of one or more hydrocarbons which are free of vinyl group in the treatment of a distillation column suitable for distilling vinyl aromatic compounds such as styrene allows to wash off the components of the distillation columns and at the same time to bring suitable heat to activate the polymer seeds present. Component B is selected to have no chemical moiety susceptible to polymerize.

For example, the vinyl aromatic compounds are or comprise styrene, and the flux comprising a passivation mixture that is passed through at least one distillation column during the passivation step comprises ethylbenzene and/or is devoid of styrene.

For example, the step of cleaning one or more distillation columns is or comprises a mechanical cleaning; with preference, the mechanical cleaning of one or more distillation columns comprises high-pressure cleaning of one or more distillation columns.

Selection of the Passivation Conditions

For example, the passivation conditions comprise a temperature which is ranging between a temperature being 10° C. above the boiling point of the vinyl aromatic compounds at pressure conditions and a temperature being at most 20° C. above the boiling point of the vinyl aromatic compounds at pressure conditions, or ranging between a temperature being 15° C. above the boiling point of the vinyl aromatic compounds at pressure conditions and a temperature being at most 20° C. above the boiling point of the vinyl aromatic compounds at pressure conditions. The passivation conditions always comprise a temperature which is superior to the temperature at which the distillation of the vinyl aromatic compounds is carried out.

For example, the passivation conditions comprise a temperature of at least 95° C.; for example, at least 100° C.; for example, at least 105° C.; for example, at least 110° C.; for example, at least 115° C.; for example, at least 120° C.

For example, the passivation conditions comprise a temperature of at most 250° C.; for example, at most 220° C.; for example, at most 200° C.; for example, at most 180° C.; for example, at most 160° C.; for example, at most 150° C. or at most 145° C.

For example, the passivation conditions comprise a temperature ranging from 90° C. to 250° C.; for example, from 95° C. to 220° C.; for example, from 100° C. to 200° C.; for example, from 105° C. to 180° C.; for example, from 110° C. to 160° C.; for example, from 115° C. to 150° C.; for example, from 120° C. to 145° C.

The choice of the temperature of the passivation step is related to the choice of the component B. For example, when the component B is or comprises ethylbenzene, the person skilled in the art would have the advantage to select a temperature ranging from 115° C. to 150° C.; for example, from 120° C. to 145° C.

The person skilled in the art may also adapt the temperature with the pressure selected for the passivation conditions. For example, when working at reduced pressure, namely below atmospheric pressure, the passivation temperature corresponds to a temperature which is below the temperature that would have been chosen if the working pressure would have been the atmospheric pressure. Thus, the passivation temperature is advantageously ranging between 90° C. and 110° C., preferably between 95° C. and 105° C.

However, the person skilled in the art may have the advantage to work minimum at atmospheric pressure (i.e., 101325 Pa) or higher, so that the passivation conditions comprises pressure conditions up to 300 kPa; with preference, the passivation conditions comprise pressure conditions preferably ranging from 90 kPa to 200 kPa; more ranging from 98 to 120 kPa, for example, from 100 to 115 kPa.

For example, said passivation conditions comprise a passivation time which is ranging from 1 to 24 hours; for example, from 2 to 20 hours; for example, from 3 to 18 hours; for example, from 5 to 15 hours.

For example, the step of passivation is performed under an atmosphere provided by one or more inert gases such as nitrogen and/or argon.

For example, the one or more distillation columns of the vinyl aromatic compounds distillation unit comprise a reboiler. The flux of the passivation mixture has a flow at the level of the reboiler that is ranging between 1 l/h and 250 l/h, preferably between 50 l/h and 100 l/h, more preferably between 60 l/h and 90 l/h, even more preferably between 65 l/h and 85 l/h.

Selection of Component A

For example, component A comprises at least one polymerisation inhibitor selected from molten sulphur, phenyl-p-phenylenediamines, phenothiazines, tert-butyl catechol (TBC), diethyl-hydroxylamine (DEHA), quinone methide (QM), 2-(3,5-di-tert-butyl-4-oxocyclohexa-2,5-dien-1-ylidene)acetonitrile (QM-CN), 2,6-di-tert-butyl-4-(methoxymethylene) cyclohexa-2,5-dienone (QM-OMe), 4-benzylidene-2,6-di-tert-butylcyclohexa-2,5-dienone (QM-Ph), butylated hydroxytoluene (BHT), butylated hydroxyanisole (BHA), 4-hydroxy-2,2,6,6-tetramethylpiperidin-1-oxyl (4-OH-TEMPO) and any mixture thereof; with preference from tert-butyl catechol (TBC), diethyl-hydroxylamine (DEHA) and any mixture thereof; more preferably component A is diethyl-hydroxylamine (DEHA).

Selection of Component B

For example, component B is steam.

For example, component B is one or more hydrocarbons devoid of vinyl group wherein one or more hydrocarbons devoid of vinyl group are or comprise one or more aliphatic saturated hydrocarbons and/or one or more aromatic compounds; with preference, at least one aromatic compound devoid of vinyl group is selected from benzene, toluene, o-xylene, m-/or xylene, p-xylene, ethylbenzene, a mixture benzene/ethylbenzene, and any mixture thereof.

Component B may be or comprises BTX; namely, benzene, toluene, o-xylene, m-xylene, p-xylene and any mixtures thereof.

Component B may be or comprises BTEX; namely, benzene, toluene, o-xylene, m-xylene, p-xylene, ethylbenzene and any mixtures thereof.

For example, aliphatic saturated hydrocarbons are one or more selected from heptane, octane, nonane, decane and any mixture thereof. For example, when a mixture benzene/ethylbenzene is selected, said mixture comprises between 10 wt. % and 30 wt. % of benzene and between 70 wt. % and 90 wt. % of ethylbenzene based on the total weight of said mixture benzene/ethylbenzene, preferably, said mixture comprises between 15 wt. % and 25 wt. % of benzene and between 75 wt. % and 85 wt. % of ethylbenzene.

For example, component B is a mixture of steam and one or more hydrocarbons devoid of vinyl group, wherein one or more hydrocarbons devoid of vinyl group are or comprise one or more aliphatic saturated hydrocarbons and/or one or more aromatic compounds; with preference, at least one aromatic compound devoid of vinyl group is selected from benzene, toluene, o-xylene, m-xylene, p-xylene, ethylbenzene, a mixture benzene/ethylbenzene, and any mixture thereof. For example, aliphatic saturated hydrocarbons are one or more selected from heptane, octane, nonane, decane and any mixture thereof. For example, when a mixture benzene/ethylbenzene is selected, said mixture comprises between 10 wt. % and 30 wt. % of benzene and between 70 wt. % and 90 wt. % of ethylbenzene based on the total weight of said mixture benzene/ethylbenzene, preferably, said mixture comprises between 15 wt. % and 25 wt. % of benzene and between 75 wt. % and 85 wt. % of ethylbenzene.

For example, when component B is a mixture of steam and one or more hydrocarbons devoid of vinyl group, the ratio between steam and the one or more hydrocarbons is ranging between 0.25 and 4, preferably between 1 and 3.

With preference, component B is one or more selected from a mixture of steam and benzene, a mixture of steam and ethylbenzene, a mixture of steam, benzene and ethylbenzene and any mixture thereof.

The one or more hydrocarbons free of vinyl group which are present in the mixture that is used to treat the distillation column are aromatics compounds free of vinyl group that can be selected from the list comprising benzene, ethylbenzene, toluene, o-xylene, m-xylene, p-xylene. More preferably, said one or more hydrocarbons free of vinyl group are selected from benzene and/or ethylbenzene, even more preferably from ethylbenzene. Indeed, since the process of the present disclosure is useful for passivating distillation column suitable for vinyl aromatic compounds, it is more efficient to use a mixture of one or more hydrocarbons belonging to the same chemical family of said vinyl aromatic compounds. Thus, in an example, when styrene is the vinyl aromatic compound to be distilled, ethylbenzene can be the hydrocarbon of choice.

Process of Purification of one or More Vinyl Aromatic Compounds

The disclosure also provides a process of purification of at least one vinyl aromatic compound that includes the cleaning process above described.

Thus, the disclosure provides a process of purification of one or more vinyl aromatic compounds, the process comprising the distillation of one or more vinyl aromatic compounds using vinyl aromatic compounds distillation unit wherein the vinyl aromatic compounds distillation unit comprises one or more distillation columns, the process comprising interrupting at least one time the distillation of one or more vinyl aromatic compounds to perform a cleaning process of the vinyl aromatic compounds distillation unit, remarkable in that the cleaning process of the vinyl aromatic compounds distillation unit is according to the first aspect; with preference, the one or more vinyl aromatic compounds is or comprises styrene.

For example, the cleaning process comprises a passivation step that is conducted at a temperature higher than the temperature at which the distillation is conducted. Indeed, working at a higher temperature allows activating relatively quickly any residual polymers and/or any polymer seeds. Once activated, they will be oxidized and decomposed during the cleaning process.

For example, a preferred vinyl aromatic compound that can be purified is styrene. The distillation unit may comprise several distillation columns for the treatment of the vinyl aromatic compound-rich stream produced. In a first column, the benzene and the toluene will be separated. Then, in a subsequent column, ethylbenzene is separated from styrene and in a third column, the styrene is further purified. Advantageously, the ethylbenzene separated in the second column can be recycled in the production process or the cleaning process.

Process of Production of a Vinyl Aromatic Compound From the Corresponding Saturated Aromatic Compound The disclosure also provides a process production of a vinyl aromatic compound from the corresponding saturated aromatic compound that includes the cleaning process and/or the purification process above described.

Thus, the disclosure provides a process of production of a vinyl aromatic compound from the corresponding saturated aromatic compound, said process is remarkable in that it comprises the following steps:
  a) providing a catalytic composition comprising one or more zeolites;
  b) providing a stream comprising a saturated aromatic compound;
  d) contacting said stream comprising a saturated aromatic compound with said catalytic composition under dehydrogenation reaction conditions comprising a temperature of at least 550° C. to obtain a vinyl aromatic compound-rich stream;
  e) performing the process of purification of at least one vinyl aromatic compound according to the second aspect on said vinyl aromatic compound-rich stream;
  f) optionally, recovering the vinyl aromatic compound from the vinyl aromatic compound-rich stream.

For example, the vinyl aromatic compound produced is styrene and the corresponding saturated aromatic compound is ethylbenzene; with preference, the stream provided in step (b) further comprises di-ethylbenzene, and the process further comprises a step (c) of removing said di-ethylbenzene from said stream provided in step (b) before contacting the stream with the catalyst composition.

For example, the one or more zeolites are selected from the group of MWW, FAU, MFI, MOR family, or zeolite beta or any mixture thereof. With preference, said one or more zeolites are selected from the group of MWW, FAU, MFI family, or zeolite beta, or any mixture thereof.

For example, when the zeolite is a zeolite from the MWW family, said zeolite is MCM-22. A particular example of a zeolite from the MWW family is a zeolite that is used in a process of ethylbenzene alkylation, said process being for example the EBMax$^{SM}$ process.

For example, when the zeolite is a zeolite from the MFI family, said zeolite is ZSM-5.

For example, when the zeolite is a zeolite selected from the FAU family, said zeolite is zeolite Y and/or USY.

For example, the catalytic composition further comprises at least one metal derivative; with preference, the metal of said at least one metal derivative is iron. For example, the catalytic composition is or comprises a ferrite, preferably a ferrite with an active surface comprising potassium iron oxide with a 1/1 atomic ratio of K/Fe, whereby iron is only in its trivalent state. Further information regarding an example of ferrite can be found in the study of Muhler M., et al. (*J. of Cata.*, 1992, 138, 413-44).

For example, said dehydrogenation reaction conditions comprise one or more of the following:
- a temperature ranging between 500° C. and 700° C., preferably between 525° C. and 675° C., more preferably between 550° C. and 650° C.; and/or
- a pressure ranging between 0.01 MPa and 100 MPa, preferably ranging between 0.1 MPa and 90 MPa, more preferably between 1 MPa and 80 MPa, even more preferably between 10 MPa and 75 MPa, most preferably between 20 MPa and 70 MPa, even most preferably between 30 MPa and 65 MPa, or between 35 MPa and 60 MPa; and/or
- a liquid hourly space velocity ranging between 0.3 $h^{-1}$ and 1.0 $h^{-1}$, preferably between 0.4 $h^{-1}$ and 0.9 $h^{-1}$ or between 0.5 $h^{-1}$ and 0.8 $h^{-1}$.

In a preferred embodiment of the disclosure, the vinyl aromatic compound is styrene and the corresponding saturated aromatic compound is ethylbenzene. Therefore, the disclosure provides a process for the production of styrene from ethylbenzene, said process being remarkable in that it comprises the following steps:
a) providing a catalytic composition comprising one or more zeolites;
b) providing a stream comprising ethylbenzene;
d) contacting said stream comprising ethylbenzene with said catalytic composition under dehydrogenation reaction conditions to obtain a styrene-rich stream;
e) performing the process of purification of at last one vinyl aromatic compound according to the second aspect on said styrene-rich stream; and
f) optionally, recovering the styrene from the styrene-rich stream.

Examples of commercially available catalytic composition for the production of styrene from ethylbenzene are StyroStar® S6-42 or StyroMax® UL3.

Advantageously, in said preferred embodiment, the stream provided in step (b) further comprises di-ethylbenzene, and the process further comprises a step (c) of removing said di-ethylbenzene from said stream provided in step (b) before contacting the stream with the catalyst composition.

Within said preferred embodiment, the stream comprising ethylbenzene provided in step (b) advantageously comprises at most 50 ppm of di-ethylbenzene, preferably at most 40 ppm, more preferably at most 30 ppm, even more preferably at most 20 ppm, most preferably at most 10 ppm or is devoid of di-ethylbenzene. Indeed, under dehydrogenation reaction conditions, p-di-ethylbenzene or m-di-ethylbenzene can be respectively converted into p-divinylbenzene or m-divinylbenzene which are polymerizable compounds since they comprise a vinyl group. O-di-ethylbenzene, under dehydrogenation reaction conditions, can be converted into naphthalene, which is a heavy component difficult to remove from a distillation column. Therefore, it is advantageous that when the stream provided in step (b) comprises di-ethylbenzene, the process comprises the step of removing said di-ethylbenzene from the said stream.

The integrated system, in which the production of styrene from ethylbenzene, followed by the purification of the styrene-rich stream according to the process of purification of at least one vinyl aromatic compound described in the present disclosure, namely in which a distillation column is first treated with a mixture comprising ethylbenzene at a passivation temperature which is at least a temperature at which the distillation column is working under distillation conditions of styrene, namely under passivation conditions comprising a passivation temperature of at least 90° C., preferably within a passivation temperature ranging between 120° C. and 145° C. under atmospheric pressure, allows rendering efficient to the production of styrene from ethylbenzene since the styrene-rich stream which comprises also unconverted ethylbenzene can be conveyed into the distillation column directly after the passage of the ethylbenzene onto the catalytic composition. The unconverted ethylbenzene will be mixed with the ethylbenzene used to treat the distillation column and will be separated at this stage, so that styrene could be properly recovered.

Test and Determination Methods

Gamma Scanning

The gamma apparatus that has been employed is the gamma apparatus Tru-Scan™ from Tracerco. A small source emitting gamma rays is placed on one side of the device. On the opposite, a radiation-sensitive electronic detector is used to measure the radiation transmitted through the column, allowing it to have a measurement through the chord of the column. The source and detector are aligned at the same elevation and simultaneously descending in small steps along a predefined part of the column. At each step, the transmitted radiation is measured by the detector and recorded on a computer. At the end of the scan, the results are represented on a graph (such as those represented on the left side of the figures) emitted by the signal measured against elevation. For a restricted window of gamma rays, the intensity of the radiation transmitted through the device is defined by the following formula: $I=I_0 e^{(-\mu \rho x)}$; wherein (I) is the radiation transmitted through the equipment and measured by the detector; ($I_o$) is the radiation transmitted through an empty device; (x) is the material thickness between the source and the detector; (ρ) is the density of the material; and (μ) is a constant named mass attenuation coefficient.

Therefore, if the distance (path inside the vessel) is maintained, the transmitted radiation is a function of the density inside the device. By performing several measurements, typically four, it is possible to detect whether the column is empty (and thus clean) or not (and thus fouled).

EXAMPLE

Styrene was produced from a stream of ethylbenzene comprising some di-ethylbenzene. The vinyl aromatic compound-rich stream produced (i.e., styrene) was subjected to a purification process comprising the distillation of styrene using one vinyl aromatic compounds distillation unit comprising a distillation column 1. However, after about 4.5 years of use, pollution of styrene with divinylbenzene (DVB) was observed due to high polymerization incidents and the distillation column 1 was fouled.

The vinyl aromatic compounds distillation unit was therefore stopped and mechanical cleaning of the distillation column 1 was operated including the high-pressure cleaning of the columns and some structured packing, such as tower internals, that was damaged by the fouling, was changed. The vinyl aromatic compounds distillation unit was stopped for 1 month.

Figure 2:
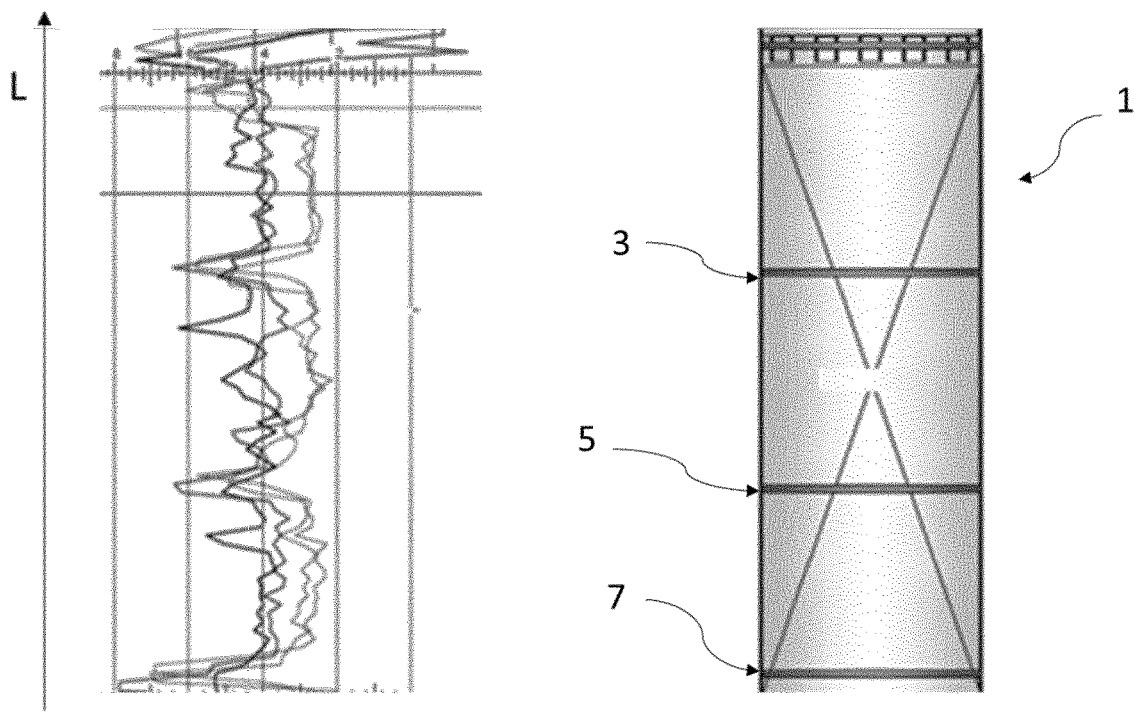
FIG. 2: Gamma scan of a fouled distillation column.

The unit was then restarted but after 2 months of running without any DVB pollution of crude styrene, the separation problem was back due to bad distribution and fouling. These problems increased till the distillation was stopped again for one month to perform the cleaning of the distillation column 1. The bad distribution and fouling are shown by the control scan of FIG. 2 (left side) wherein gaps can be seen between the different curves.

Figure 3:
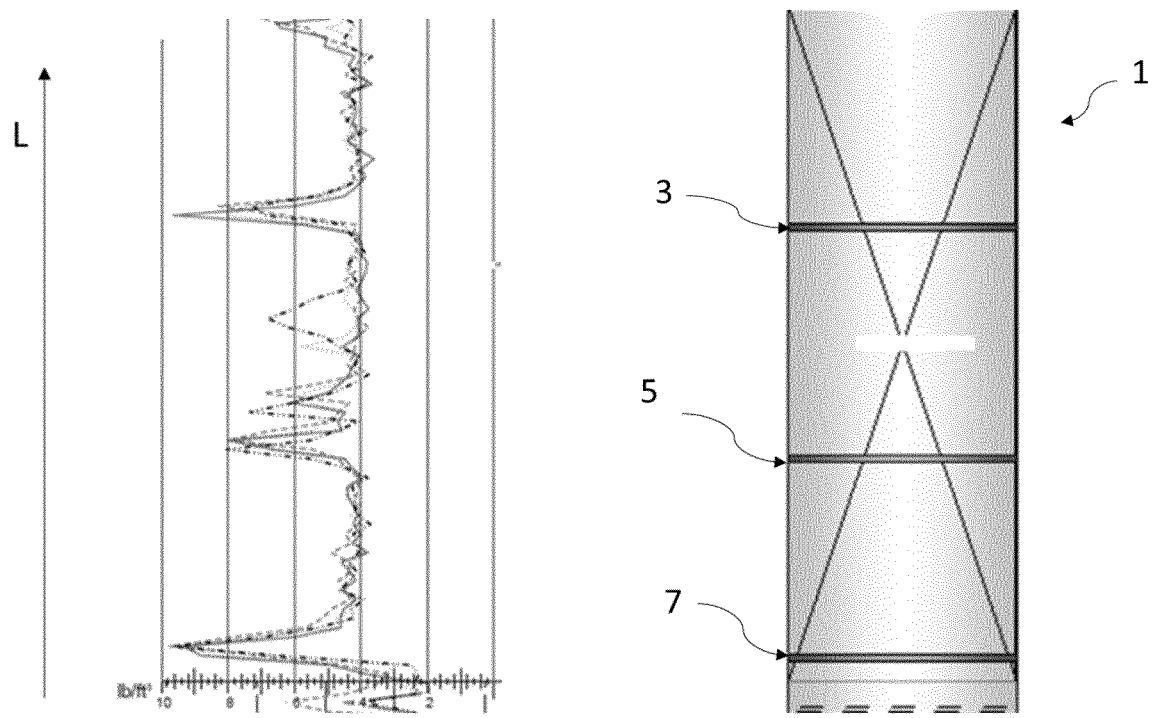
FIG. 3: Gamma scan of distillation column after performing the cleaning process of a vinyl aromatic compounds distillation unit in accordance with the present disclosure.

The cleaning process performed this time was including a passivation step after the step of cleaning, as defined in the present disclosure. The step of cleaning was mechanical including the high-pressure cleaning of column 1 and the change of the packing. The step of passivation was performed by injecting, 3 kg of DEHA as component A, into each of the reboilers (9, 19). The total amount of DEHA was distributed into the distillation column 1 via both the reflux loop and the reboiler loop. A baseline pH check has been done just before the injection of DEHA, indicating a pH ranging between 4 and 5. The correct circulation of component A was indeed checked by collecting a sample at the bottom of the distillation column and measuring the pH using wetted pH strip tests. A pH ranging between 8 and 9 was an indication of the correct circulation of DEHA within the distillation column 1. Additional injection of DEHA can be made in the case where the pH falls below the range of 8 and 9. Once the correct circulation of DEHA within the distillation column has been ascertained, ethylbenzene, as component B, is injected into the reboiler loop. The injection of ethylbenzene is continuous and amounts to 4500 kg. The flow of the passivation mixture comprising DEHA and ethylbenzene, taken at the level of one of the reboilers (9, 19), was measured to be 70 l/h. After having purged the distillation column 1, said column 1 was restarted and the control scan is showing a good situation. The control scan is illustrated in FIG. 3 (left side) wherein all density lines are grouped showing a good distribution within column 1. The big peaks that can be shown correspond to the location of the horizontal distribution trays (3, 5, 7) that are schematized on the right side of the figures. Since then (16 months later), the distillation unit is still performing well.

The invention claimed is:

1. Cleaning process of a vinyl aromatic compounds distillation unit wherein the vinyl aromatic compounds distillation unit comprises one or more distillation columns (1), the process comprises a step of cleaning one or more distillation columns (1) and is characterized in that the step of cleaning one or more distillation columns (1) is followed by a step of passivation of at least one distillation column (1) wherein a flux comprising a passivation mixture is passed through at least one distillation column (1) under passivation conditions comprising a temperature of at least 90° C. and a pressure up to 300 kPa, wherein the passivation mixture comprises a component A being one or more polymerisation inhibitors and a component B selected from steam and/or one or more hydrocarbons devoid of vinyl group that are one or more aliphatic saturated hydrocarbons and/or one or more aromatic compounds.

2. The cleaning process according to claim 1, characterized in that the passivation mixture comprises from 0.01 wt. % to 2.00 wt. % of component A based on the total weight of the passivation mixture, the remaining being made of component B.

3. The cleaning process according to claim 1, characterized in that the passivation conditions comprise a temperature which is ranging between a temperature being 10° C. above the boiling point of the vinyl aromatic compounds and a temperature being at most 20° C. above the boiling point of the vinyl aromatic compounds; and/or in that the passivation conditions comprise a temperature of at least 100° C. and/or at most 250° C.

4. The cleaning process according to claim 1, characterized in that the passivation conditions comprise a pressure ranging from 98 to 120 kPa; and/or in that the step of passivation is performed under an atmosphere provided by one or more inert gases.

5. The cleaning process according to claim 1, characterized in that at least one aromatic compound devoid of vinyl group is selected from benzene, toluene, o-xylene, m-xylene, p-xylene, ethylbenzene, a mixture benzene/ethylbenzene, and any mixture thereof; and/or in that the one or more aliphatic saturated hydrocarbons are one or more selected from heptane, octane, nonane, decane, and any mixture thereof.

6. The cleaning process according to claim 1, characterized in that component A comprises at least one polymerisation inhibitor selected from molten sulphur, phenyl-p-phenylenediamines, phenothiazines, tert-butyl catechol, diethyl-hydroxylamine, quinone methide, 2-(3,5-di-tert-butyl-4-oxocyclohexa-2,5-dien-1-ylidene) acetonitrile, 2,6-di-tert-butyl-4-(methoxymethylene)cyclohexa-2,5-dienone, 4-benzylidene-2,6-di-tert-butylcyclohexa-2,5-dienone, butylated hydroxytoluene, butylated hydroxyanisole, 4-hydroxy-2,2,6,6-tetramethylpiperidin-1-oxyl and any mixture thereof.

7. The cleaning process according to claim 6, wherein the component A polymerisation inhibitor is selected from the group consisting of tert-butyl catechol, diethyl-hydroxylamine and any mixture thereof.

8. The cleaning process according to claim 1, characterized in that the flux comprising a passivation mixture that is passed through at least one distillation column (1) during the passivation step is devoid of vinyl aromatic compounds.

9. The cleaning process according to claim 1, characterized in that the vinyl aromatic compounds are selected from styrene, alpha-methyl styrene, divinylbenzene, polyvinyl benzene and any mixture thereof.

10. The cleaning process of claim 9, wherein the vinyl aromatic compounds are or comprise styrene.

11. The cleaning process according to claim 1, characterized in that the step of passivation is conducted during a time ranging from 1 to 24 hours.

12. The cleaning process according to claim 11 wherein the step of passivation is conducted during a time ranging from 5 to 15 hours.

13. The cleaning process according to claim 1, characterized in that the step of cleaning one or more distillation columns (1) is or comprises a mechanical cleaning.

14. The cleaning process according to claim 13, characterized in that the step of cleaning one or more distillation columns (1) is or comprises pressure washing of one or more distillation columns (1).

15. Process of purification of one or more vinyl aromatic compounds, the process comprising the distillation of one or more vinyl aromatic compounds using vinyl aromatic compounds distillation unit wherein the vinyl aromatic compounds distillation unit comprises one or more distillation columns (1), the process comprising interrupting at least one time the distillation of one or more vinyl aromatic compounds to perform a cleaning process of the vinyl aromatic compounds distillation unit, characterized in that the cleaning process of the vinyl aromatic compounds distillation unit is according to claim 1.

16. The process of purification of claim 15, characterized in that the cleaning process comprises a passivation step that is conducted at a temperature higher than the temperature at which the distillation is conducted.

17. Process of production of a vinyl aromatic compound from the corresponding saturated aromatic compound, said process is characterized in that it comprises the following steps:
- a) providing a catalytic composition comprising one or more zeolites;
- b) providing a stream comprising a saturated aromatic compound;
- d) contacting said stream comprising a saturated aromatic compound with said catalytic composition under dehydrogenation reaction conditions comprising a temperature of at least 550° C. to obtain a vinyl aromatic compound-rich stream;
- e) performing the process of purification of at least one vinyl aromatic compound according to claim 11 on said vinyl aromatic compound-rich stream;
- f) optionally, recovering the vinyl aromatic compound from the vinyl aromatic compound-rich stream.

18. The process of production according to claim 17, characterized in that the vinyl aromatic compound produced is styrene and the corresponding saturated aromatic compound is ethylbenzene; with preference, the stream provided in step (b) further comprises di-ethylbenzene, and the process further comprises a step (c) of removing said di-ethylbenzene from said stream provided in step (b) before contacting the stream with the catalyst composition.

19. The process of production according to claim 17, characterized in that one or more zeolites are selected from FAU, MFI, or MOR family and/or in that the catalytic composition further comprises at least one transition metal.

20. The process of claim 15 wherein the one or more vinyl aromatic compounds is or comprises styrene.

* * * * *